United States Patent
Chung et al.

(10) Patent No.: US 8,497,241 B2
(45) Date of Patent: Jul. 30, 2013

(54) WNT10-DERIVED PEPTIDE AND USE THEREOF

(75) Inventors: Young Ji Chung, Yongin-si (KR); Eun Mi Kim, Gunpo-si (KR); Sang Su Song, Seoul (KR); Kyoung Mi Cho, Cheonan-si (KR)

(73) Assignee: Caregen Co., Ltd., Gunpo-si (KR)

( * ) Notice: Subject to any disclaimer, the term of this patent is extended or adjusted under 35 U.S.C. 154(b) by 0 days.

(21) Appl. No.: 13/393,370

(22) PCT Filed: Nov. 24, 2009

(86) PCT No.: PCT/KR2009/006933
§ 371 (c)(1),
(2), (4) Date: May 10, 2012

(87) PCT Pub. No.: WO2011/027941
PCT Pub. Date: Mar. 10, 2011

(65) Prior Publication Data
US 2012/0245086 A1 Sep. 27, 2012

(30) Foreign Application Priority Data
Sep. 1, 2009 (KR) ........................ 10-2009-0081817

(51) Int. Cl.
*A61K 38/08* (2006.01)
*A61P 17/00* (2006.01)
*A61P 17/14* (2006.01)
*A61P 35/00* (2006.01)
*A61P 19/10* (2006.01)
*A61P 19/02* (2006.01)
*A61P 3/10* (2006.01)
*A61Q 19/08* (2006.01)
*C07K 7/06* (2006.01)

(52) U.S. Cl.
USPC ......... 514/6.9; 514/16.7; 514/16.8; 514/16.9; 514/18.6; 514/18.8; 514/19.2; 514/20.7; 514/21.6; 530/328

(58) Field of Classification Search
None
See application file for complete search history.

(56) References Cited

U.S. PATENT DOCUMENTS
5,824,789 A * 10/1998 Van Den Berg ............. 536/23.5
2002/0114772 A1 8/2002 Morgan et al.
2006/0115460 A1 6/2006 Naughton FOREIGN PATENT DOCUMENTS
WO WO 2006/105109 A2 10/2006
WO WO 2006/105109 A3 10/2006

OTHER PUBLICATIONS

Ouji, Y, et al. Wnt-10b secreted from lymphocytes promotes differentiation of skin epithelial cells. Biochem Biophys Res Com. 2006; vol. 342: 1063-1069.*
Ouji, Y, et al. Effects of Wnt-10b on hair shaft growth in hair follicle cultures. Biochem Biophys Res Com. 2007; vol. 359: 516-522.*
Christodoulides et al. Adipogenesis and WNT signalling. Trends in Endocrinology & Metabolism. 2009; vol. 20: 16-24.*
Qurrat-ul-Ain et al. Integrative analyses of conserved WNT clusters and their co-operative behaviour in human breast cancer. Biomed Info. 2011; vol. 7: 339-346.*
Ouji et al., "Effects of Wnt-10b on Hair Shaft Growth in Hair Follicle Cultures," Biochem. Biophys. Res. Commun. 359:516-522, 2007.
Ouji et al., "Wnt-10b Promotes Differentiation of Skin Epithelial Cells in Vitro," Biochem. Biophys. Res. Commun. 342:28-35, 2006.
Sick et al., "WNT and DKK Determine Hair Follicle Spacing Through a Reaction-Diffusion Mechanism," Science 314:1447-1450, 2006.
International Search Report from International Application No. PCT/KR2009/006933, dated Oct. 26, 2010 (date of completion of search) and Nov. 1, 2010 (date of mailing of report).

* cited by examiner

*Primary Examiner* — Karlheinz R Skowronek
*Assistant Examiner* — Schuyler Milton
(74) *Attorney, Agent, or Firm* — Clark & Elbing LLP

(57) ABSTRACT

The present invention relates to a WNT10-derived peptide, a composition for improving hair loss and skin conditions using the same, and a composition for treating a WNT10 signal transduction pathway-related disorder and DKK-1 protein-induced disorder the same. WNT10-derived peptide of the present invention possesses identical or similar activities to natural-occurring WNT10, and has much higher stability and skin penetration potency than natural-occurring WNT10. Therefore, the composition containing the present peptide not only shows excellent effects on improvement in hair loss (for example, promotion of hair growth or production of hair), but also has superior efficacies on treatment of a WNT10 signal transduction pathway-related disorder and a DKK-1 protein-induced disorder. In addition, the outstanding activity and stability of the present peptide described above may be greatly advantageous in application to pharmaceutical compositions, quasi-drugs and cosmetics.

19 Claims, 20 Drawing Sheets

Control

Peptide treatment

WNT10-DERIVED PEPTIDE AND USE THEREOF

CROSS-REFERENCE TO RELATED APPLICATIONS

This application is the U.S. national stage filing under 35 U.S.C. §371 of international application PCT/KR2009/006933, filed Nov. 24, 2009, which claims benefit of Korean Patent Application 10-2009-0081817, filed Sep. 1, 2009.

BACKGROUND OF THE INVENTION

1. Field of the Invention

The present invention relates to a WNT10-derived peptide, a composition for improving hair loss and skin conditions using the same, and a composition for treating a WNT10 signal transduction pathway-related disorder and DKK-1 protein-induced disorder using the same.

2. Description of the Related Art

Hair follicle is a peculiar skin organ of mammals, which is developed from the bottom of primitive epidermis into much internal skin layer. The plug of cells known as follicle or dermal papilla exists in the base of the hair follicle (Stenn and Paus, *Physiol. Rev.*, 81: 449 (2002)), and papilla is essential in normal circulation of the hair follicle (Oliver, *Embryol. Exp. Morph.* 15: 331 (1966); Oliver, *Embryol. Exp. Morph.* 16: 231 (1967)) and in growth of the hair shaft. The hair shaft is a thread-shaped epithelial cells that are composed of keratin filaments and filament-aggregating proteins tightly attached thereto.

Human hair follows a growth cycle with three distinct phases: anagen, catagen, and telogen phases. The hair growth cycle is regulated by hormones or many growth factors. Severe stress or malnutrition may advance the catagen and telogen phases, leading to severe hair loss (alopecia) (Vladimir A. Botchkarev, *American Journal of Pathology*, 162 (3): 709-712 (2003)). In male pattern baldness, the hair follicles at the front and top of the scalp are sensitive to androgen, which causes the follicles to miniaturize, thereby resulting in hair loss. Briefly, excessive secretion of androgen activates 5-α reductase which causes testosterone to be converted to dihydrotestosterone (DHT). Subsequently, DHT reduces the number of thick dark terminal hairs by shortening a period of hair growth and by miniaturing hair follicles, leading to hair loss. It has been supposed that about 20% of hair loss women suffer from a few disorders called as "female pattern baldness" which the hair often becomes thinner at the top of the scalp. In addition, hair loss broadens with aging. For example, severe hair loss may be caused from different disorders such as cicatricial alopecia or scar conditions including burns or compression injury. Whatever is the cause, while woman power in the workforce has been enhanced and men have cared about their appearance, hair loss may have remarkable psychological, social and sexual impacts as well as loss of pride and self-respect. Although various medicaments have been used to treat hair loss, they are too expensive or give very different adverse effects among individuals. Additionally, it is necessary to take these drugs in a constant manner. In this connection, it is one of serious drawbacks that hair loss may be caused by stopping them. Meanwhile, another demerit is that their efficacies and side effects may be quitely different between individuals.

Raw materials utilized in cosmetic products have the advantage of being inexpensive, whereas do not give good results since they are composed of plant extract-derived components. To overcome shortcomings in view of biostability, efficacy or cost, there has been developed a method that WNT10-derived peptides having activities identical to a natural-occurring WNT10 may be produced in an inexpensive manner by a chemical synthesis method, and a nano peptide product having a superior efficacy and skin permeability using a nanosome technology, compared with a whole protein. The peptide permits to induce the proliferation and differentiation of stem cell present in hair follicle on skin to produce hair root, leading to develop new hair follicle. In addition, the peptide allows activation of WNT-β-catenin signal pathway to express genes inducing hair growth even under conditions that WNT10 pathway is inactivated by DKK-1, a hair loss gene, produced by DHT. Furthermore, the peptide effectively facilitates anagen during which hair growth is active, and potently inhibits transition of anagen to catagen in hair follicle cycle caused by various environmental factors, resulting in inhibition of hair loss. In addition, the peptide shows beneficial effects on growth and healthy of normal hair through supplying nutrients to hair. It has been known up to now that two commercial drugs (minoxidil and finasteride) may delay only additional hair loss. However, no actual medicaments may have been useful to induce regeneration of new hair follicle in practice. Many scalp cosmetics for preventing hair loss have been commercially available in the market, for example including: (a) a product including a plant extract derived from sophora, hot pepper, Swertia herb, Morus alba, mulberry leaf, ginseng, licorice, peony, foxglove, fennel, Japanese cornel, garlic, and so forth; (b) a composition containing xanthines and growth hormones for not only improving cellular metabolism suppressed by excess dihydrotestosterone (DHT) but also facilitating hair growth through hair loss inhibition and hair regeneration induced by growth hormones; (c) a product containing minerals, vitamins and extracts of green tea, rosemary, mugwort or licorice, which supplies nutrients to the scalp and hair for preventing hair loss and promoting hair growth; and (d) a male pattern baldness product mixing the substances such as vitamin B, vitamin C, vitamin D, vitamin E, nicotinic acid, pantothenic acid, biotin, folic acid, etc. with plant extracts, which inhibits 5-α reductases to suppress production of DHT during androgen metabolism and to help hair metabolism by have been developed. However, they have hardly influence on the production of new hair. As another example, a research group of the Jikei University School of Medicine in Tokyo, Japan has developed the product using corosolic acid known to be effective in diabetes, which inhibits 5-α reductases and exhibits an excellent effect on hair growth.

Many factors are associated with each other in the growth and degeneration of hair. For hair production, the present researchers have studied serial growth factors having an activity for: (a) promoting proliferation of keratinocyte which is most important for hair root production; (b) inducing differentiation of hair; (c) supplying nutrients to the vicinity of hair; and (d) activating vascular endothelial growth factors. Of them, human-derived WNT10 specifically affects hair development by transferring a signal to a cell. WNT10 signal transduction pathway is activated by an interaction between secreted WNT10 protein and Frizzled protein which is a receptor thereof. In this connection, LDL receptor-related proteins (LRP5 and LRP6) function as a co-receptor (Clin Cancer Res 2007; 13 (14) Jul. 15, 2007, WNT Signaling Pathway and Stem Cell Signaling Network). Downstream effects in WNT10 signal transduction pathway include participation of Axin-β-catenin-GSK3 β complex through activation of DVL (Disheveled) protein and Akt (Fukumoto et al., *J. Biol. Chem.*, 276: 17479-17483 (2001)). Afterwards, GSK3 β is inactivated by phosphorylation, resulting in inhibition of phosphorylation and degradation of β-catenin. Accumulated β-catenins are translocated to a nucleus and then interact with transcription factors of the lymphoid enhancer factor-T cell factor (LEF-TCF), permitting to induce transcription of target genes. The resulting proteins may be a critical role for hair growth and differentiation, and allow new hair cell to be produced. Furthermore, they decrease activities of DHT produced by male hormone (androgen) to suppress hair loss.

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THIS INVENTION

For developing peptides having actions identical to natural-occurring human WNT10 protein as well as having more enhanced stability and skin penetration than natural-occurring WNT10 protein, the present inventors have prepared and screened a multitude of human WNT10-derived peptides. As a result, the present inventors have discovered WNT10-derived peptides having superior stability and skin penetration as well as excellent physiological activities (e.g., improvement in hair loss, promotion of cell growth, facilitation of fibronectin expression, etc.) on the basis of the amino acid sequence of natural-occurring WNT10, eventually accomplishing the present invention.

Accordingly, it is one object of this invention to provide a peptide containing the amino acid sequence of SEQ ID NO:1.

It is another object of this invention to provide a composition for improving hair loss.

It is still another object of this invention to provide a composition for improving skin conditions.

It is still another object of this invention to provide a composition for improving or treating a WNT10 signal transduction pathway-related disorder.

It is further still another object of this invention to provide a composition for treating a DKK-1 protein-induced disorder.

Other objects and advantages of the present invention will become apparent from the following detailed description together with the appended claims and drawings.

For developing peptides having actions identical to natural-occurring human WNT10 protein as well as having more enhanced stability and skin penetration than natural-occurring WNT10 protein, the present inventors have prepared and screened a multitude of human WNT10-derived peptides. As a result, the present inventors have discovered WNT10-derived peptides having superior stability and skin penetration as well as excellent physiological activities (e.g., improvement in hair loss, promotion of cell growth, facilitation of fibronectin expression, etc.) on the basis of the amino acid sequence of natural-occurring WNT10.

The present inventors have developed novel economical analogues by preparing peptides with actions identical to natural-occurring human WNT10 protein to overcome conventional drawbacks such as: (a) additional time-consuming refolding process to obtain active WNT10 protein in spite of excellent activities of WNT10 protein; (b) complicated purification procedure to remove *E. coli*-derived contaminants; (c) problematic permeability to hair barrier because of stability and high molecular weight; and (d) difficulty in practical application due to high cost.

The peptide of the present invention includes an amino acid sequence selected from the group consisting of WNT10-derived amino acid sequences. Preferably, the peptide in this invention consists essentially of the amino acid sequence of SEQ ID NO:1. The term used herein "peptide" refers to a linear molecule formed by linking between amino acid residues through peptide bonds.

The peptides of the present invention may be prepared by conventional chemical synthesis processes known to one of skill in the art, in particular, solid-phase synthesis techniques (Merrifield, *J. Amer. Chem. Soc.* 85: 2149-54 (1963); Stewart, et al., *Solid Phase Peptide Synthesis,* 2nd. ed., Pierce Chem. Co.: Rockford, 111 (1984)).

The peptides of the present invention may be prepared by primarily predicting a portion of capable of binding to a receptor protein through random partial synthesis of several portions in WNT10 protein and then optimizing an amino acid sequence of the predicted portion. Afterwards, the candidate peptides having the most excellent activity are screened to isolate the peptides of this invention.

The peptide of SEQ ID NO:1 not only has actions similar to natural-occurring WNT10 protein but also shows growth factor activities via binding to a receptor.

According to a preferable embodiment, the present peptide facilitates cell proliferation in keratinocytes and fibroblasts. According to a preferable embodiment, the present peptide promotes fibronectin expression.

In addition, the peptide of this invention exhibits an activity for activating WNT signaling pathway. According to a preferable embodiment, the peptide of the present invention transfers β-catenin into a nucleus.

The peptides of this invention per se have higher stability than natural-occurring WNT20 protein, and its modification enables to have much higher stability.

Preferably, the peptides of this invention have at their N-terminal a protection group selected from the group consisting of acetyl group, fluorenyl methoxy carbonyl group, formyl group, palmitoyl group, myristyl group, stearyl group and polyethylene glycol (PEG).

According to a preferable embodiment, the peptides of this invention may have a protection group selected from the group consisting of acetyl group, fluorenyl methoxy carbonyl group, formyl group, palmitoyl group, myristyl group, stearyl group and polyethylene glycol (PEG). Therefore, the protection groups of the present peptides contribute to much higher stability than the modification of naturally occurring WNT20 protein.

The modifications of peptides described above greatly increase the stability of the peptides of this invention. The term used herein "stability" refers to in vivo stability and storage stability (e.g., storage stability at room temperature) as well. The protection group described above protects the peptides from the attack of protease in vivo.

In another aspect of this invention, there is provided a composition for treating or improving hair loss, containing as an active ingredient the aforementioned peptide of this invention.

In still another aspect of this invention, there is provided a composition for improving skin conditions, containing as an active ingredient the aforementioned peptide of this invention.

Since the present composition comprises the growth factor-related peptide of this invention as active ingredients described above, the common descriptions between them are omitted in order to avoid undue redundancy leading to the complexity of this specification.

According to a preferable embodiment, the present composition further includes the peptide having the amino acid sequence of SEQ ID NO:2 or SEQ ID NO:3, or both peptides.

According to a preferable embodiment, the treatment or improvement of hair loss by the present peptide is promotion of hair growth or production of hair.

As demonstrated in Examples below, the peptides of the present invention have stimulatory activity to cell proliferation in keratinocytes and fibroblasts and facilitate β-catenin signaling as a representative signal pathway of WNT10 protein. It could be verified that the peptide of the present invention allows WNT signal pathway to be active in spite of the presence of DKK-1 as a WNT inhibitor. In addition, fibronectin expression as a target gene of WNT was enhanced by the present peptide. Furthermore, it could be demonstrated that the peptide of the present invention contributes to enhanced fibronectin expression even in the presence of DKK-1. According to animal experiments based on the above-mentioned results, it could be appreciated that the peptide of the present invention significantly promotes hair growth. Therefore, the composition of the present invention has excellent effects on hair growth and the improvements in skin conditions.

According to a preferable embodiment, the improvement in the skin conditions by the present peptide is improvement in wrinkle or skin elasticity, prevention of skin aging, improvement in skin moisture, removal of wound or regeneration of skin.

In still another aspect of this invention, there is provided a composition for improving or treating a WNT10 signal transduction pathway-related disorder, containing as an active ingredient the aforementioned peptide of this invention.

In further still another aspect of this invention, there is provided a composition for treating a DKK-1 protein-induced disorder, containing as an active ingredient the aforementioned peptide of this invention.

Since the present composition comprises the growth factor-related peptide of this invention as active ingredients described above, the common descriptions between them are omitted in order to avoid undue redundancy leading to the complexity of this specification.

According to a preferable embodiment, the WNT10 signal transduction pathway-related disorder includes an eye disorder, a lipid-modulated disorder, a bone disorder or a tumor disorder, and more preferably, a bone disorder or a tumor disorder.

According to a preferable embodiment, the bone disorder is selected from the group consisting of a disease associated with bone development, a bone fracture, a senile bone loss, chondrodystrophia, hypercalcemia, hyperostosis, osteogenesis imperfect, osteomalacia, osteomyelitis, osteoporosis, Paget's disease of bone, osteoarthritis and rachitis.

According to a preferable embodiment, the tumor disorder includes colorectal carcinoma, breast carcinoma or melanoma.

According to a preferable embodiment, the lipid-modulated disorder is selected from the group consisting of cardiopathy, familial lipoprotein lipase deficiency, Type III hyperlipoproteinemia, familial hypercholesterolemia, familial hypertriglyceridemia, multiple lipoprotein-type hyperlipoproteinemia, lipid increase by dialysis and/or diabetes, and familial apoprotein CII deficiency.

According to a preferable embodiment, the DKK-1 protein-induced disorder includes diabetes or muscle recovery and regeneration, and the diabetes is associated with treatment of insulin resistance and hypoglycemia.

According to a preferable embodiment, the composition is a pharmaceutical composition containing: (a) a pharmaceutically effective amount of the growth factor-related peptide of the present invention; and (b) a pharmaceutically acceptable carrier.

The term used herein "pharmaceutically effective amount" refers to an amount enough to show and accomplish efficacies and activities of the growth factor-related peptide of this invention.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

According to the conventional techniques known to those skilled in the art, the pharmaceutical composition according to the present invention may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

According to a preferable embodiment, the composition is a cosmetic composition containing: (a) a cosmetically effective amount of the growth factor-related peptide of the present invention; and (b) a cosmetically acceptable carrier.

The term used herein "cosmetically effective amount" refers to an amount enough to accomplish efficacies on improvements in skin conditions described hereinabove.

The cosmetic compositions of this invention may be formulated in a wide variety of forms, for example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray. Specifically, the cosmetic compositions of this invention may be formulated in the form of skin softner, nutrient liquid, nutrient cream, massage cream, essence, eye cream, cleansing cream, cleansing foam, cleansing water, pack, spray or powder.

Where the cosmetic composition is in the form of paste, cream or gel, it may include animal and vegetable fats, waxes, paraffins, starch, tragacanth, cellulose derivatives, polyethylene glycols, silicones, bentonites, silica, talc, zinc oxide or mixtures of these substances.

In the formulation of powder or spray, it may include lactose, talc, silica, aluminum hydroxide, calcium silicate, polyamide powder and mixtures of these substances. Spray may additionally comprise the customary propellants, for example, chlorofluorohydrocarbons, propane/butane or dimethyl ether.

The formulation of solution and emulsion may include solvent, solubilizer and emulsifier, for example water, ethanol, isopropanol, ethyl carbonate, ethyl acetate, benzyl alcohol, benzyl benzoate, propylene glycol, 1,3-butylglycol, oils, glycerol fatty esters, polyethylene glycol and fatty acid esters of sorbitan.

The formulation of suspension may contain liquid diluents, for example water, ethanol or propylene glycol, suspending agents, for example ethoxylated isosteary alcohols, polyoxyethylene sorbitol esters and poly oxyethylene sorbitan esters, micocrystalline cellulose, aluminum metahydroxide, bentonite, agar and tragacanth or mixtures of these substances.

The formulation of cleansing compositions with surfactant may contain aliphatic alcohol sulfate, aliphatic alcohol ether sulfate, sulfosucinnate monoester, isothinate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives, ethoxylated glycerol fatty acid ester or mixtures of these ingredients.

Furthermore, the cosmetic compositions of this invention may contain auxiliaries as well as peptides as active ingredients and carriers. The non-limiting examples of auxiliaries include preservatives, antioxidants, stabilizers, solubilizers, vitamins, colorants, odor improvers or mixtures of these substances.

The features and advantages of the present invention will be summarized as follows:

(i) WNT10-derived peptide of the present invention possesses identical or similar activities to natural-occurring WNT10;

(ii) the peptides of the present invention have much higher stability and skin penetration potency than natural-occurring WNT10;

(iii) therefore, the composition containing the present peptide not only shows excellent effects on improvement in hair loss (for example, promotion of hair growth or production of hair), but also has superior efficacies on treatment of a WNT10 signal transduction pathway-related disorder and a DKK-1 protein-induced disorder; and (iv) the outstanding activity and stability of the present peptide described above may be greatly advantageous in application to pharmaceutical compositions, quasi-drugs and cosmetics.

Figure 1:
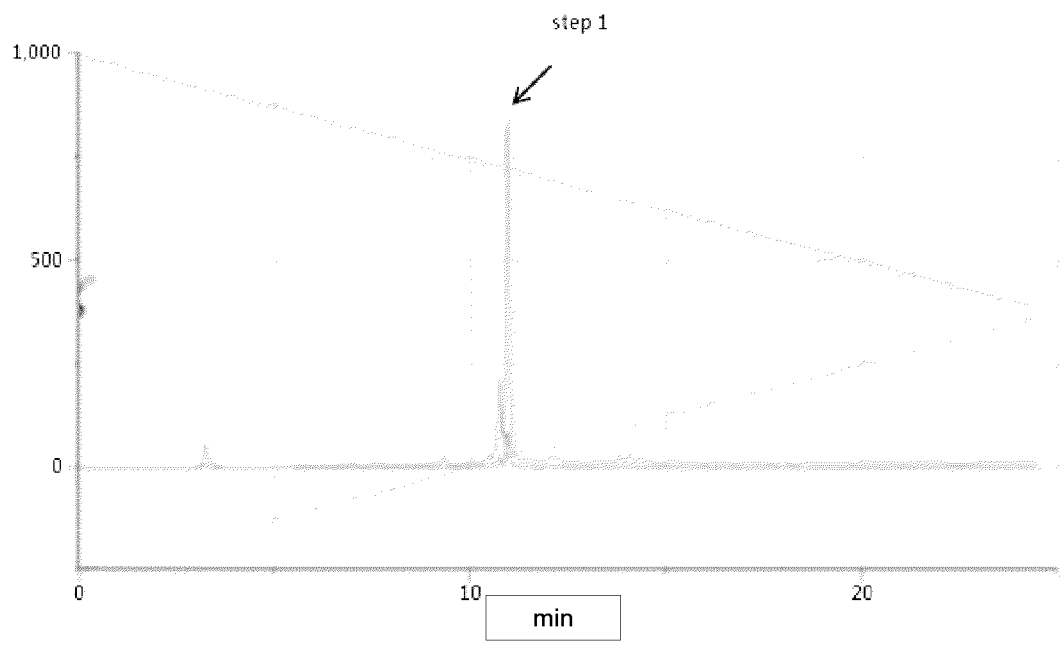
FIG. 1 represents results of HPLC (high performance liquid chromatography) analysis of the peptide of SEQ ID NO:1 prepared in Preparation Examples.

The present invention will now be described in further detail by examples. It would be obvious to those skilled in the art that these examples are intended to be more concretely illustrative and the scope of the present invention as set forth in the appended claims is not limited to or by the examples.

EXAMPLES

Preparation Example 1

Synthesis of $NH_2$-Gln-Thr-Arg-Val-Gln-Arg-Cys-His-Cys-OH (SEQ ID NO:1)

700 mg of chloro trityl chloride resin (CTL resin, Nova Biochem Cat No. 01-64-0021) were introduced into a reactor, to which 10 ml of methylene chloride (MC) were added, followed by agitation for 3 min. After removing solution, 10 ml of dimethylformamide (DMF) were added to the resultant and then agitation was carried out for 3 min, after which the solvent was removed. 10 ml of dichloromethane solution were added to the reactor and 200 mmole of Fmoc-Cys(trt)-OH (Bachem, Swiss) and 400 mmole of DIEA (N,N'-diisopropyl ethylamine) were then added to the reactor, after which the mixture was dissolved by agitation and reaction was then undertaken with agitating for 1 hr. After washing, methanol and DIEA (2:1) dissolved in DCM (dichloromethane) were reacted with the resin for 10 min, and then the resultant was washed using excess of DCM/DMF (1:1). After removing the solution, 10 ml of DMF were added to the resultant and agitation was performed for 3 min, followed by removing the solvent. 10 ml of a deprotection solution (20% piperidine/DMF) were added to the reactor and agitated for 10 min at room temperature, followed by removing the solution. After adding the same volume of the deprotection solution, the reaction was undertaken for 10 min and solution was removed, followed by washing sequentially with DMF (3 times), MC (1 times) and DMF (1 times) to yield Cys(trt)-CTL resins. 10 ml of DMF solution was added to a new reactor and then 200 mmole of Fmoc-His(trt)-OH (Bachem, Swiss), 200 mmole of HoBt and 200 mmole of Bop were added, followed by agitation for solubilization. 400 mmole of DIEA was added to the reactor twice as a fraction and agitation was carried out for at least 5 min to dissolve all solid contents. The dissolved amino acids solution was introduced into the reactor containing the deprotected resin and reaction was undertaken with agitating for 1 hr at room temperature. Following the removal of the reaction solution, the resultant was agitated three times (each for 5 min) with DMF solution to remove unreacted residuals. A small amount of the reacted resin was taken to evaluate extent of reactions by Ninhydrine test. Using the deprotection solution, the deprotection was performed twice in the same manner as described above to yield His(trt)-Cys(trt)-CTL resin. After washing with DMF and MC, further Ninhydrine test was carried out and the sequential attachments of amino acids below were performed as described above. Based on the amino acid sequence designed by the present inventors, Fmoc-Cys(trt), Fmoc-Arg, Fmoc-Gln(trt), Fmoc-Val, Fmoc-Arg, Fmoc-Thr, Fmoc-Gln (trt) and Fmoc-Arg(pbf) were sequentially attached to resins. Fmoc-protecting group was removed by thoroughly incubating with the deprotection solution twice for 10 min. For acetylation, acetic anhydride, DIEA and HoBt were incubated with the peptidyl resins for 1 hr. The prepared peptidyl resins were washed three times with DMF, MC and methanol, respectively, and gradually dried under nitrogen atmosphere, after which it was completely vacuum-dried under $P_2O_5$. The dried resins were reacted with 30 ml of a leaving solution [containing 95% trifluroacetic acid (TFA), 2.5% distilled water, 2.5% thioanisole] for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was completely dried under nitrogen atmosphere to yield 0.65 g of unpurified peptide 1, $NH_2$-Arg-Gln-Thr-Arg-Val-Gln-Arg-Cys-His-Cys-OH (yield rate; 92.6%). The molecular weight of the final product was determined as 1287.1 (theoretical MW: 1286.5) using a mass analyzer.

Preparation Example 2

Synthesis of Other Peptides

The peptides of SEQ ID NO:2 and SEQ ID NO:3 were synthesized as processes described in Preparation Example 1. The amino acid sequence of the aforementioned peptides is as follows: SEQ ID NO:2, Ac-Tyr-Lys-Ser-Lys-Lys-Gly-Gly-Trp-Thr-His (Ac-YKSKKGGWTH); and SEQ ID NO:3, Glu-Leu-Ile-Glu-His-linker-Arq-Pro-Ala-Asp (ELIEH-linker-RPAD; linker, Gly-Gly-Gly).

TABLE 1

| SEQ ID NO | Amino acid sequence | Analyzed values (mass analyzer) | |
| --- | --- | --- | --- |
| | | Analyzed values | Theoretical values |
| 1 | RQTRVERCHC | 1287.1 | 1286.5 |
| 2 | Ac-YKSKKGGWTH | 1233.8 | 1233.4 |
| 3 | ELIEH-linker-RPAD | 1250.9 | 1250.35 |

Experimental Example 1

Influence of Peptides on Cell Growth

In order to evaluate three peptides prepared in Preparation Examples 1-2 whether they have similar activities of growth factor, SRB (Sulforhodamine B; Sigma-Aldrich) colorimetric assay was carried out using HaCaT kerationcytes (Korean Cell Line Bank) and NIH3T3 fibroblasts (Korean Cell Line Bank) according to Rizzino et al. method (Rizzino, et al. *Cancer Res.*, 48: 4266 (1988)).

HaCaT ketatinocytes and NIH3T3 fibroblasts were cultured in 250 ml-flasks containing EMEM (Eagle's minimal essential media; Gibco, USA) supplemented with 10% FBS (fetal bovine serum; Sigma). Cells cultured were treated with 1% trypsin solution to detach cells from the bottom of culture flasks and centrifuged to collect cell pellets. After cells were resuspended in EMEM not containing FBS, its aliquot ($3 \times 10^3$ cells) was added to each well of 96-well plates and cultured under 5% $CO_2$ for 24 hr at 37° C. After 24-hr culture, the medium was changed with a fresh medium without serum and cells were incubated with empty sample (for normalization), three peptides synthesized (1 ng/ml, 10 ng/ml, 100 ng/ml, 1 μg/ml and 10 μg/ml) and peptide complex (1 μg/ml) aseptically dissolved in 10% DMSO for 72 hr under the same conditions as described above. After removing supernatants, cells were fixed with ethanol and then washed three times using PBS (phosphate buffered saline), followed by incubation with SRB solution. Cells were sufficiently washed with 1% acetic acid and observed under a microscope to find living cell condition. In addition, absorbance at 590 nm was measured to analyze cell viability. Meanwhile, after culturing under the same conditions, the tissue was immunostained by an immunohistochemical assay with ki-67 antibody (SantaCruz, USA) and the amount of ki-67 protein as a cell proliferation marker was observed.

Figure 2A:
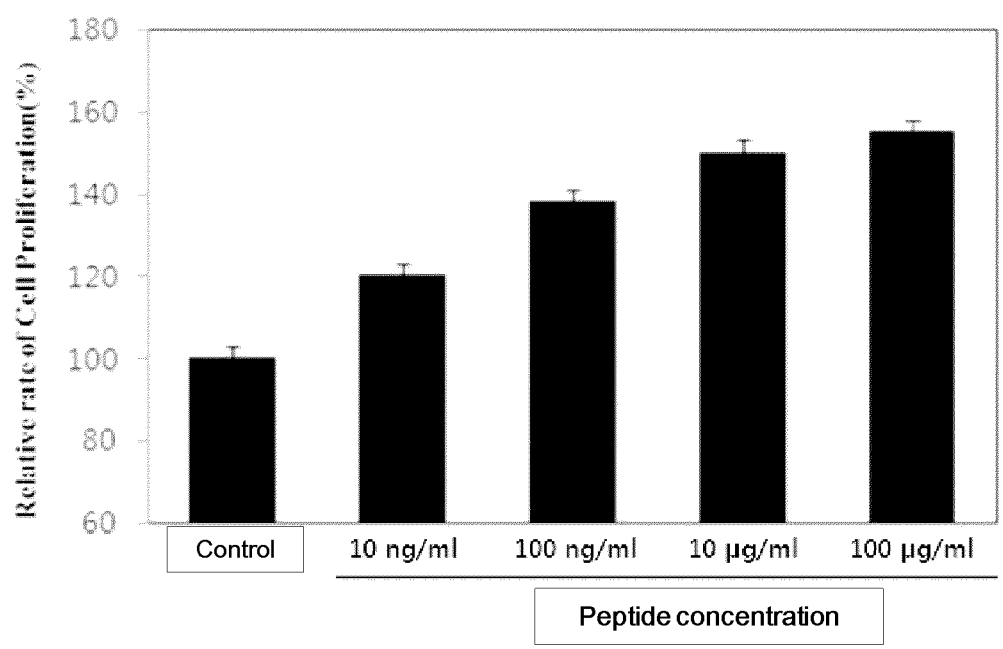
FIG. 2a is a graph representing a stimulatory effect on the growth of keratinocytes treated with the peptide prepared in Preparation Examples.
Figure 2B:
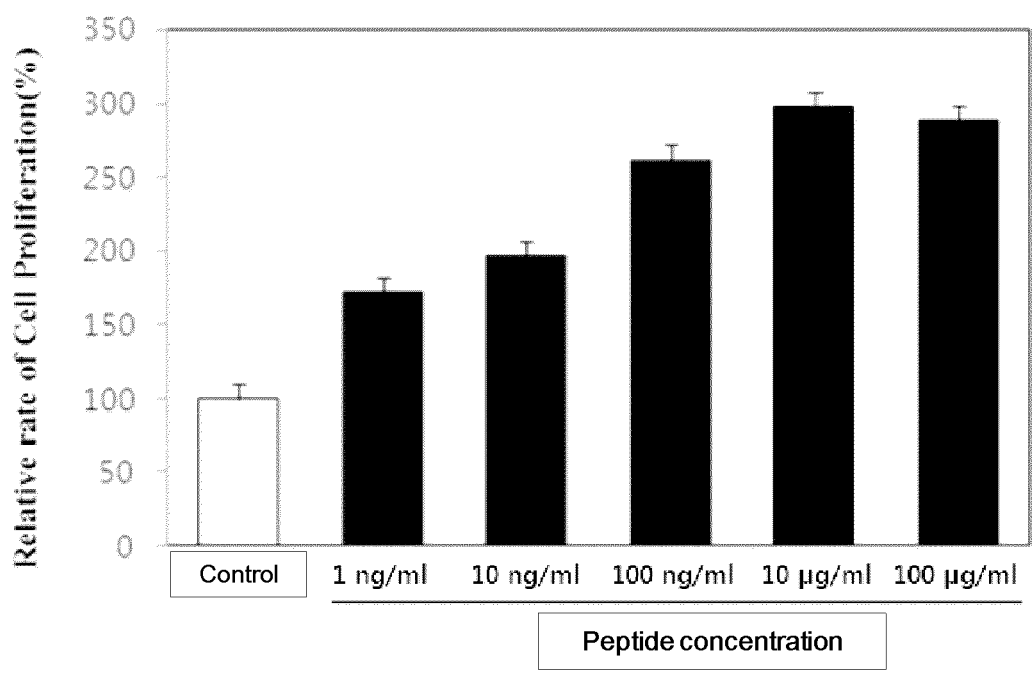
FIG. 2b is a graph representing a stimulatory effect on the growth of fibroblasts treated with the peptide prepared in Preparation Examples.

FIG. 2 demonstrates that the peptide of the present invention notably increases the growth of keratinocytes (FIG. 2a) and fibroblasts (FIG. 2b).

Figure 3:
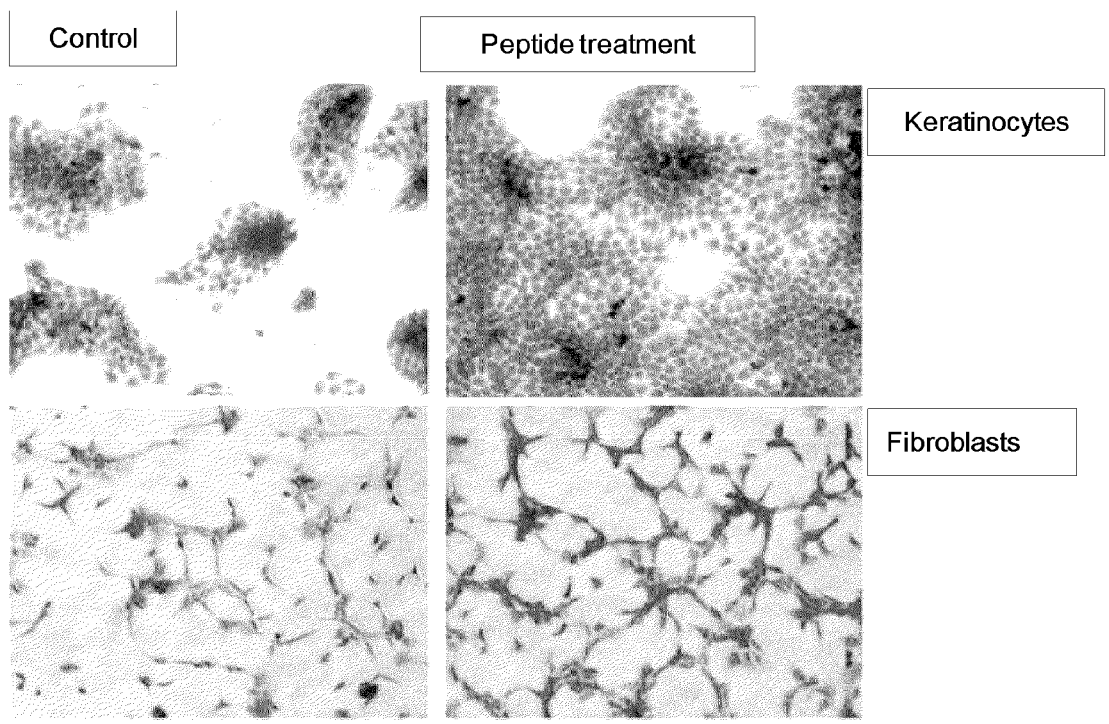
FIG. 3 is a microscope image demonstrating effects of the peptide of the present invention to promote the growth of keratinocytes and fibroblasts.

FIG. 3 is a result representing that change of cell shape is observed under a microscope after cells were treated with the present peptide for 72 hr. It could be appreciated that the peptide of the present invention promotes proliferation of keratinocytes and fibroblasts, and changes their morphological shapes.

Figure 4:
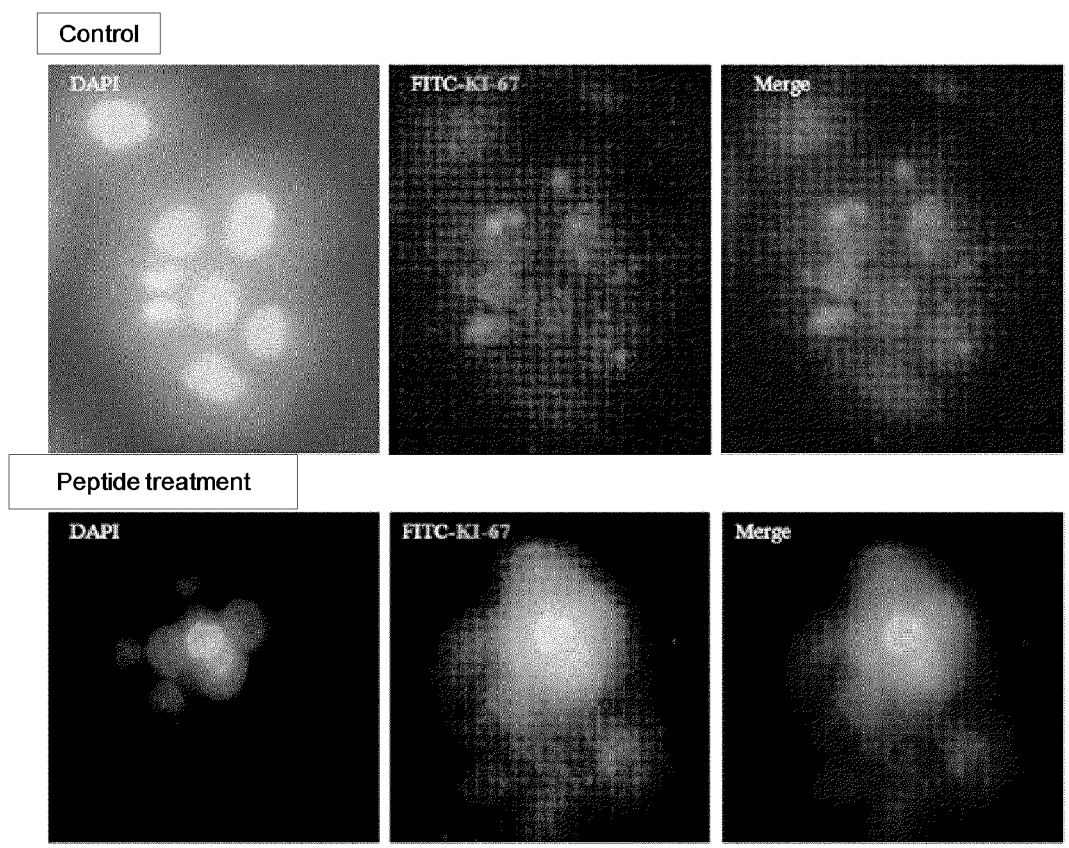
FIG. 4 shows an immunostaining image representing that the expression of Ki-67 protein (a cellular marker for proliferation) is remarkably enhanced by the treatment with the peptide of the present invention.

FIG. 4 shows that the expression of Ki-67 protein (a cellular marker for proliferation) is remarkably enhanced in keratinocytes by the treatment with the peptide of the present invention.

Figure 5A:
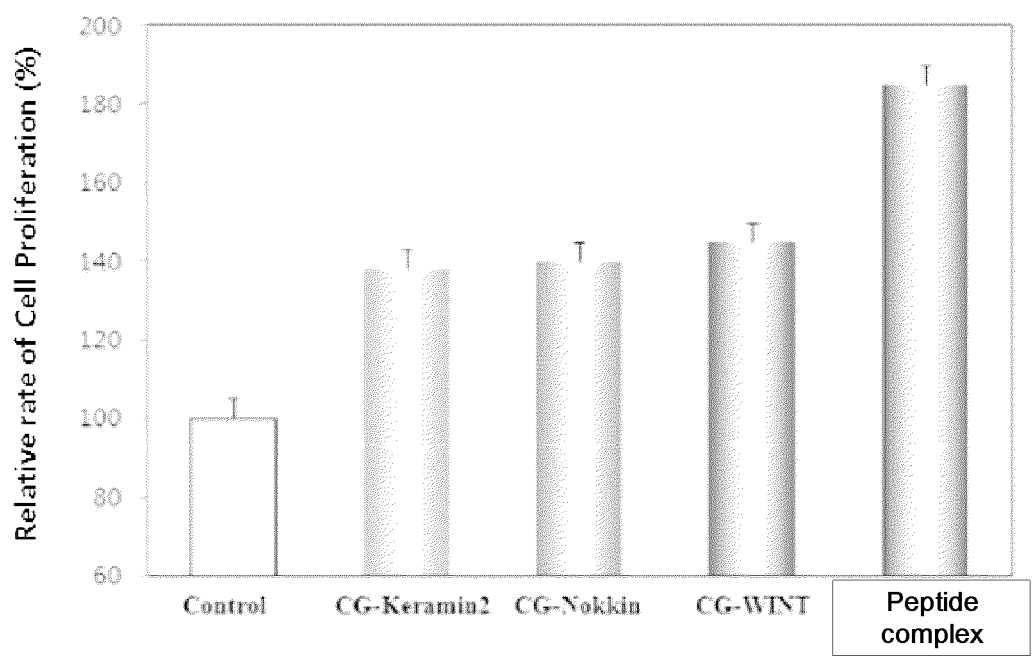
FIG. 5a is a graph representing much more enhanced cell proliferation in keratinocytes treated with peptide complex than in those treated with each peptide prepared in Preparation Examples.
Figure 5B:
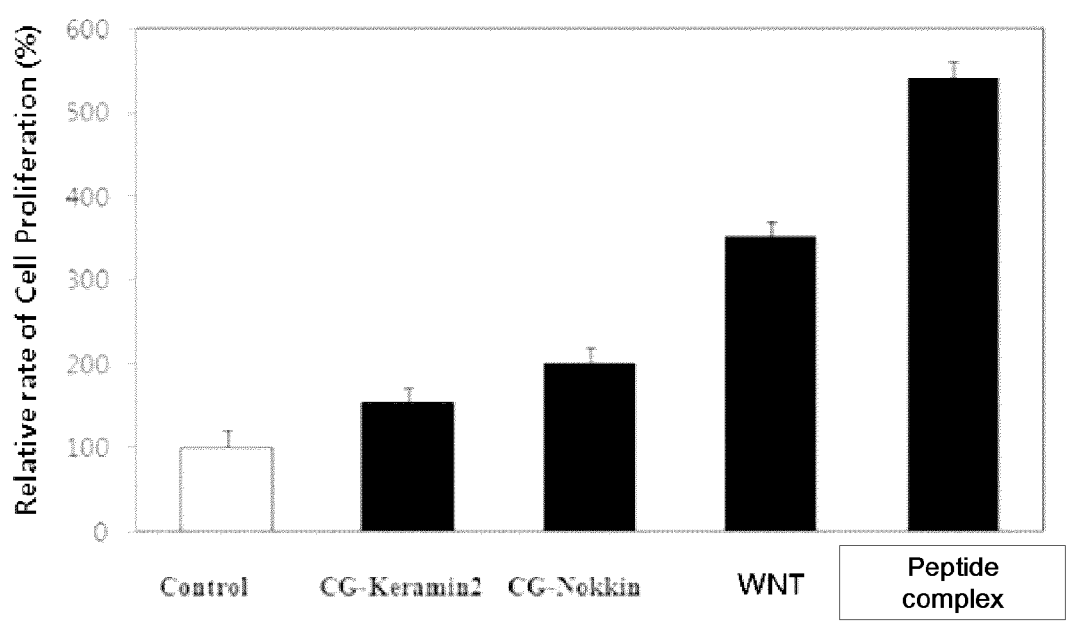
FIG. 5b is a graph representing much more elevated cell proliferation in fibroblasts treated with peptide complex than in those treated with each peptide prepared in Preparation Examples.

FIG. 5 evaluates on growth of keratinocytes (FIG. 5a) and fibroblasts (FIG. 5b) after treatment with peptide. As shown in FIG. 5a and FIG. 5b, it could be demonstrated that cell proliferation in keratinocytes and fibroblasts treated with peptide complex was much more enhanced than those treated with each peptide.

Experimental Example 2

Influence of Peptides on Elevated Amount of β-Catenin

Figure 6A:
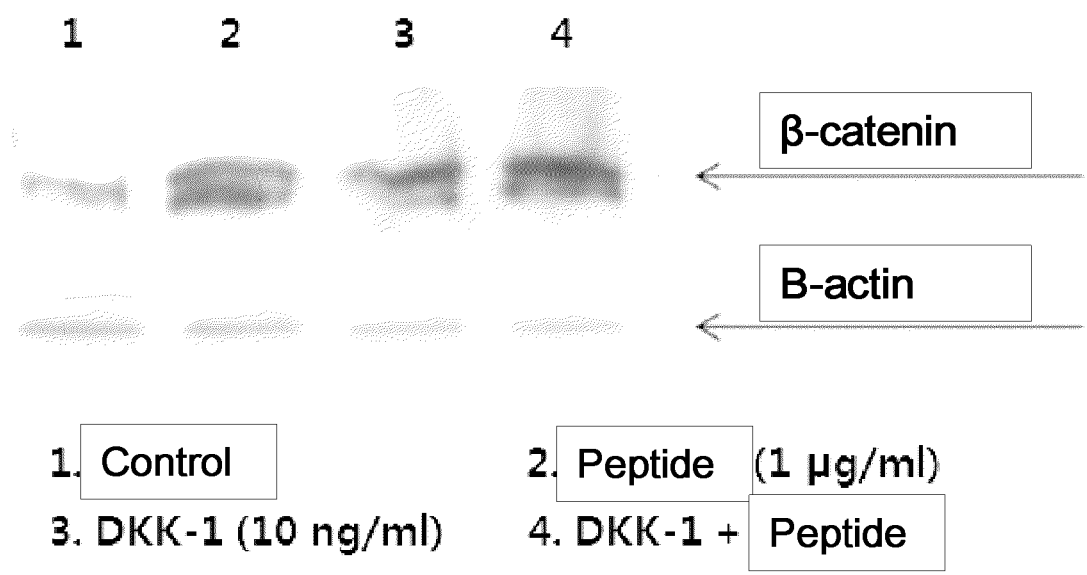
FIG. 6a shows a Western blot analysis result which measures changes of β-catenin expression by the present peptide. It was shown that the expression of β-catenin reduced by DKK-1 (a WNT inhibitor and hair loss gene) is restored and enhanced by addition of the present peptide.

HaCaT kerationcytes cultured for 48 hr were incubated with the peptides synthesized in preparation Example 1 for 5 hr. The expression level of β-catenin was examined, which is an essential signal molecule to promote hair growth as a representative signaling of WNT protein. The amount of β-catenin was measured by Western blot analysis using an antibody against β-catenin (SantaCruz, USA). In addition, it was observed by an immunohistochemical assay using the same whether β-catenin is translocated into a nucleus. The peptide of the present invention significantly elevated the expression level of β-catenin in keratinocyts. First of all, it was shown that β-catenin activity is observed by treatment with the peptide of the present invention in spite of the presence of DKK-1 as a WNT inhibitor and a β-catenin signaling inhibitor (FIG. 6a). In the immunohistochemical assay to evaluate whether the peptide functions to transfer β-catenin to nucleus, it could be demonstrated that the present peptide contributes to translocation of β-catenin from cytosol to nucleus. Besides, 3-catenin activities were also observed in cytosol as β-catenin is still present in cytosol (FIG. 6b).

FIG. 6a represents enhancement of β-catenin expression by adding the present peptide and shows re-increase of the expression of β-catenin even in treatment with both DKK-1 protein and the present peptide.

Figure 6B:
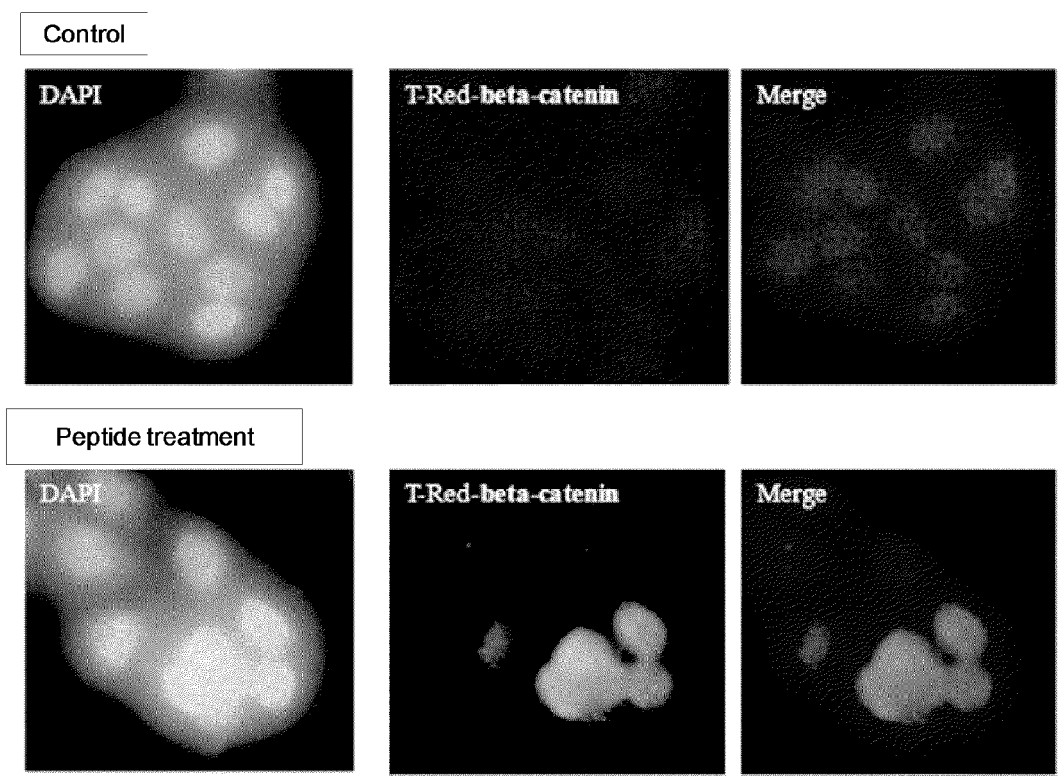
FIG. 6b is an immunostaining image representing elevated activity of β-catenin by the peptide of the present invention.

FIG. 6b is a result observed using an immunohistochemical assay, representing translocation of β-catenin to a nucleus.

Figure 7:
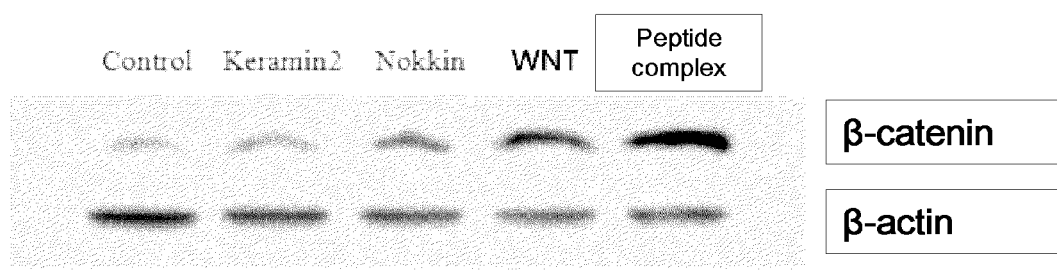
FIG. 7 is a Western blot analysis result representing still significantly stimulatory effect on β-catenin expression by peptide complex compared with each peptide prepared in Preparation Examples.
Figure 8:
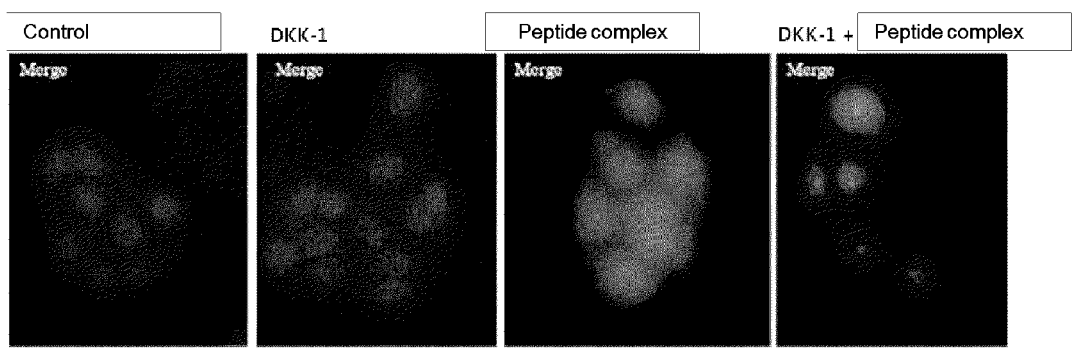
FIG. 8 shows a Western blot analysis result representing that the present peptide induces elevated activity of β-catenin, and the peptide complex highly significantly enhances β-catenin activity compared with each peptide prepared in Preparation Examples.

As shown in FIGS. 7 and 8, β-catenin expression by peptide complex was elevated much higher than that by each peptide.

Taken together in results of experimental Examples 1 and 2, it could be appreciated that the peptides of the present invention exerts excellent effects on promotion of hair growth and inhibition of hair loss, and also has an anti-aging activity.

Experimental Example 3

Influence of Peptides on Production of Fibronectin

To verify whether the peptides synthesized in preparation Example 1 enhances the expression of fibronectin as a WNT target protein, NIH3T3 fibroblasts ($4 \times 10^3$ cells) was added to each well of 96-well plates and cultured under 5% $CO_2$ for 24 hr at 37° C. After 24-hr culture, the medium was changed with a fresh medium without serum and cells were treated with empty sample (for normalization), three peptides synthesized (1 μg/ml) and peptide complex (1 μg/ml) aseptically dissolved in 10% DMSO for 3 hr, 10 hr, 24 hr or 48 hr under the same conditions as described above. After 72 hr incubation, the cell culture was collected and the expression level of fibronectin was measured using Fibronectin ELISA kit (R&D systems, USA).

Figure 9A:
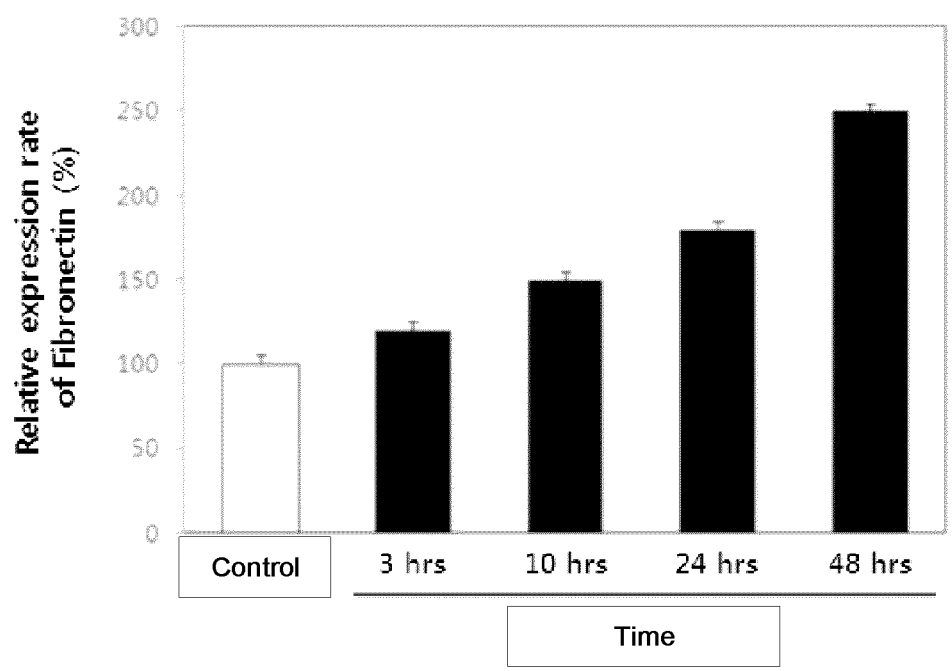
FIG. 9a is a graph representing that fibronectin expression is gradually elevated by each peptide prepared in Preparation Examples with the lapse of time.
Figure 9B:
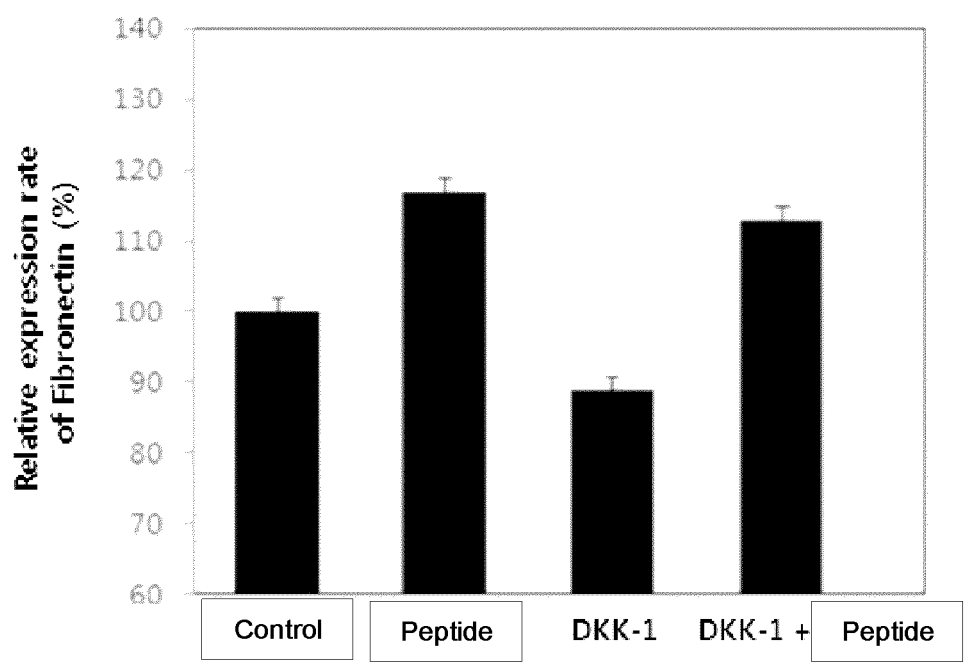
FIG. 9b represents a graph measuring changes of fibronectin expression by the present peptide. It was shown that the expression of fibronectin inhibited by DKK-1 (a WNT inhibitor and hair loss gene) was restored and enhanced by addition of the present peptide.

As demonstrated in FIG. 9a, the peptides of the present invention were revealed to elevate the level of fibronectin in fibroblasts with the lapse of time. In addition, after DKK-1 protein was treated and cultured under the same conditions, the expression level of fibronectin was examined. As shown in FIG. 9b, the expression level of fibronectin was restored and enhanced even in treatment with both DKK-1 protein and the present peptide.

FIG. 9a is a graph measuring the expression of fibronectin by treatment with the peptide of the present invention for determined time, demonstrating that fibronectin expression was gradually elevated by each peptide with the lapse of time.

FIG. 9b shows that the fibronectin expression inhibited by DKK-1 (a WNT inhibitor and hair loss gene) is recovered by addition of the present peptide. Consequently, reduction of fibronectin expression was restored with treatment of the peptide of the present invention under the same conditions as described in FIG. 9a.

Figure 10:
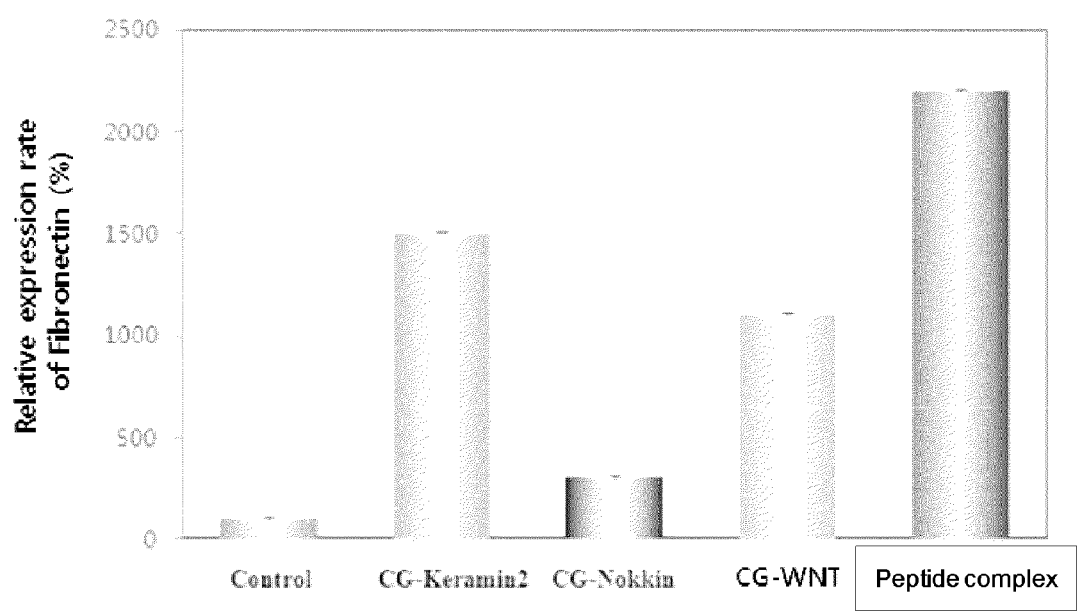
FIG. 10 is a graph of Western blot analysis representing still significantly enhanced effect on fibronectin expression by peptide complex compared with each peptide prepared in Preparation Examples.

As illustrated in FIG. 10, the expression level of fibronectin by 72 hr-treatment with peptides was elevated compared with control group, respectively, and the most elevated fibronectin expression was observed in the group treated with peptide complex.

Taken together, these results demonstrate that the peptides of the present invention induces WNT-β-catenin signaling pathway despite the presence of DKK-1 protein known to a WNT inhibitor and hair loss gene, contributing to promotion of hair growth, inhibition of hair loss and anti-aging.

Experimental Example 4

Evaluation of Heat Stability of the Prepared Peptides

Figure 11:
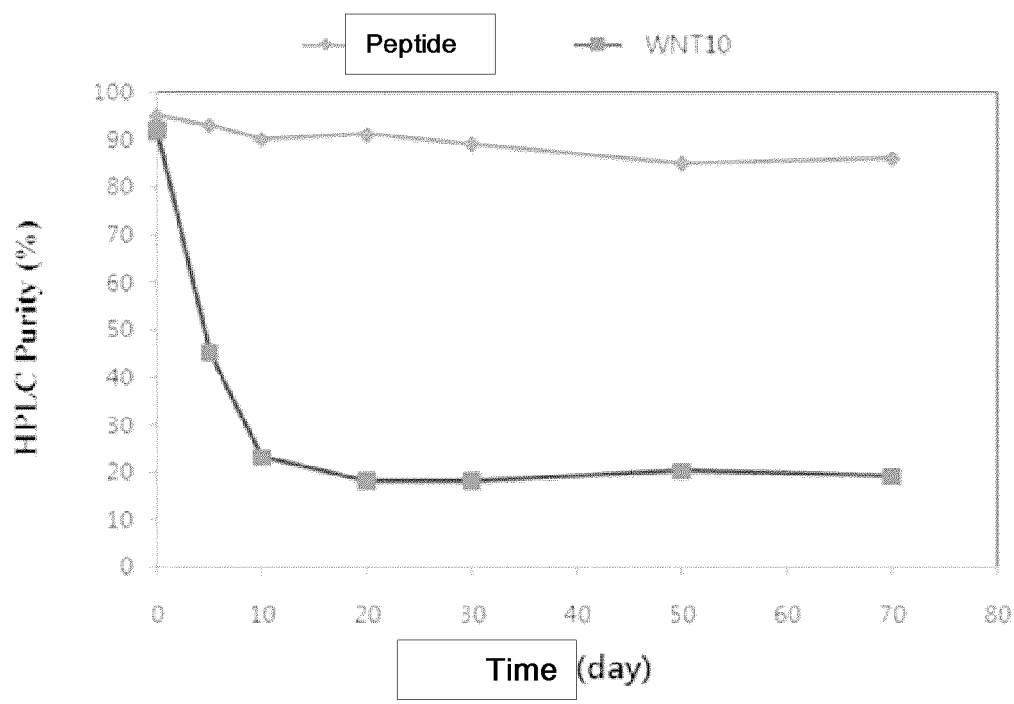
FIG. 11 represents results measuring heat stability of the peptide of this invention and naturally occurring WNT10 protein.

Each the peptide prepared in Preparation Example 1 and a standard product of growth factor (WNT10; NIBSC, UK) was dissolved in a phosphate buffer to a concentration of 0.1 mg/ml. The prepared solutions (1 ml) were introduced into glass vials and kept to stand at 37° C. Afterwards, the solutions were taken on days 0, 5, 10, 20, 30, 40 and 70, and centrifuged for removal of denatured peptides or proteins, followed by quantification using HPLC (FIG. 11).

Experimental Example 5

Analysis of Effects of Peptides on Mouse Hair Growth

Figure 12:
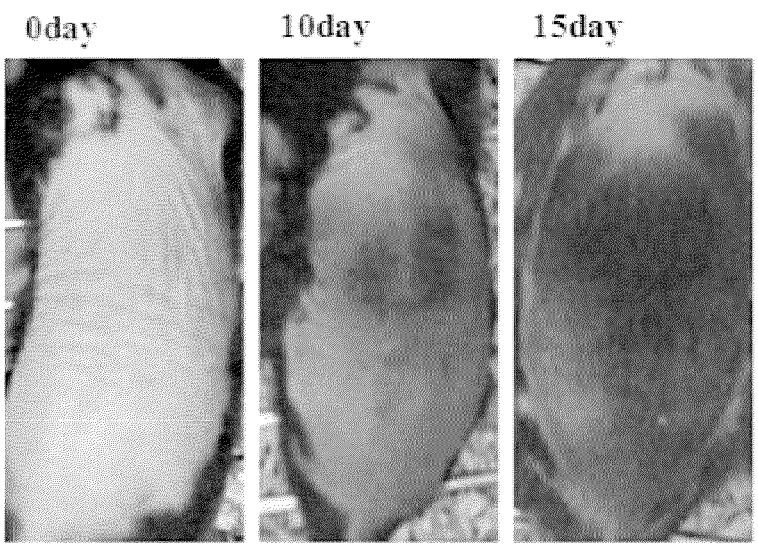
FIG. 12 represents that the peptide of the present invention has an activity for promoting hair growth on mouse back skin.
Figure 12:
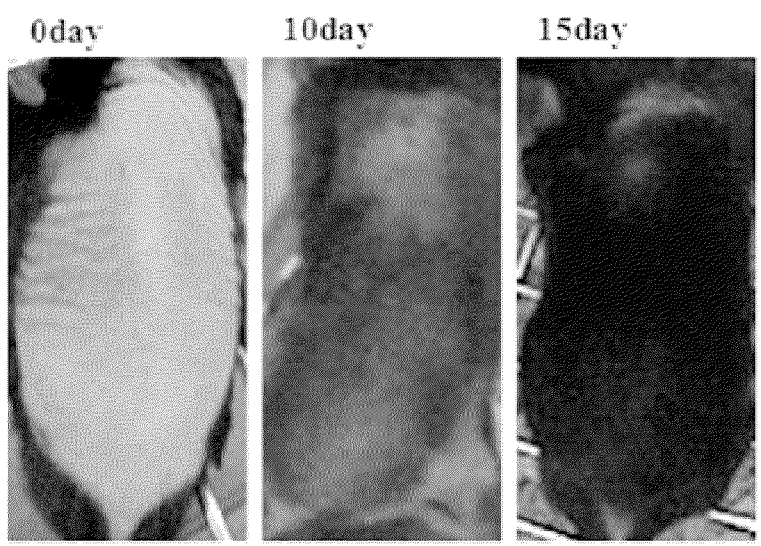

The peptide synthesized in Preparation Example 1 was formulated into nanosome. Afterwards, the back of C57BL/6 mouse was partially removed and then the skin was topically administered with the nanosome twice every day for 15 days. At 9 days-treatment, growing hair was observed in mouse back skin, and the amount of hair in mouse back skin were much significantly enhanced at 15 days-treatment compared with a control group (FIG. 12).

Experimental Example 6

Analysis of Effects of Peptide Complex on Protein Expression in Hair Follicle During Hair Follicle Culture Hair follicle of Balb/C mouse hair was dissected with a surgical mess and washed with ethanol, followed by additionally washing with PBS and DMEM culture solution. Hereafter, hair follicles were incubated with 5 μg/ml of each peptide complex dissolved in DMEM culture solution, and cultured under 5% $CO_2$ for 5 days at 37° C. After 5 days-culture, hair follicles were prepared as a paraffin block and each tissue treated with control, peptide complex, DKK-1, and DKK-1 and peptide complex was stained and compared using H&E staining (FIGS. 13a-13d).

Figure 13A:
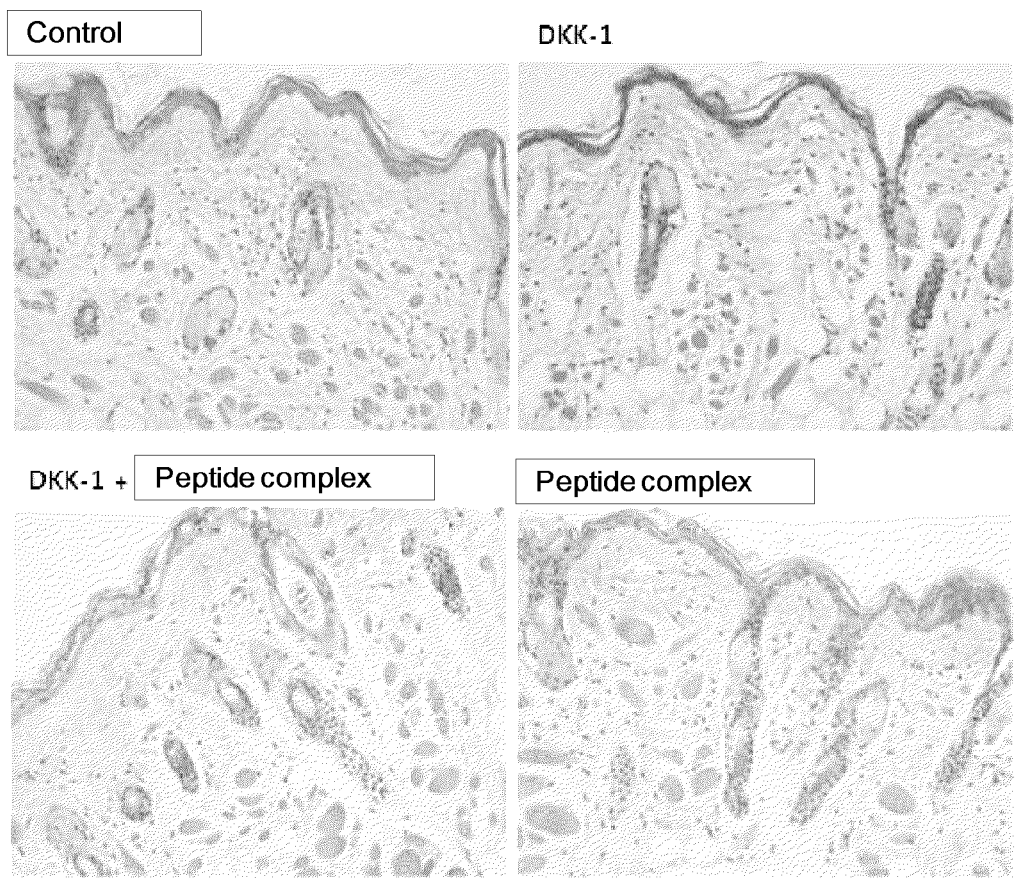
FIG. 13a shows an immunostaining image representing that in mouse hair follicle culture production of hair follicles is facilitated by the peptide complex of the present invention and hair follicles degenerated by DKK-1 protein are restored and developed by simultaneous treatment with DKK-1 and the present peptide complex.

FIG. 13a represents that DKK-1-induced degeneration of hair follicles was suppressed with the peptide complex of the present invention. It could be confirmed that hair follicles in control are degenerated by DKK-1, whereas hair follicles treated with both DKK-1 and the present peptide complex are not degenerated but produced.

Figure 13B:
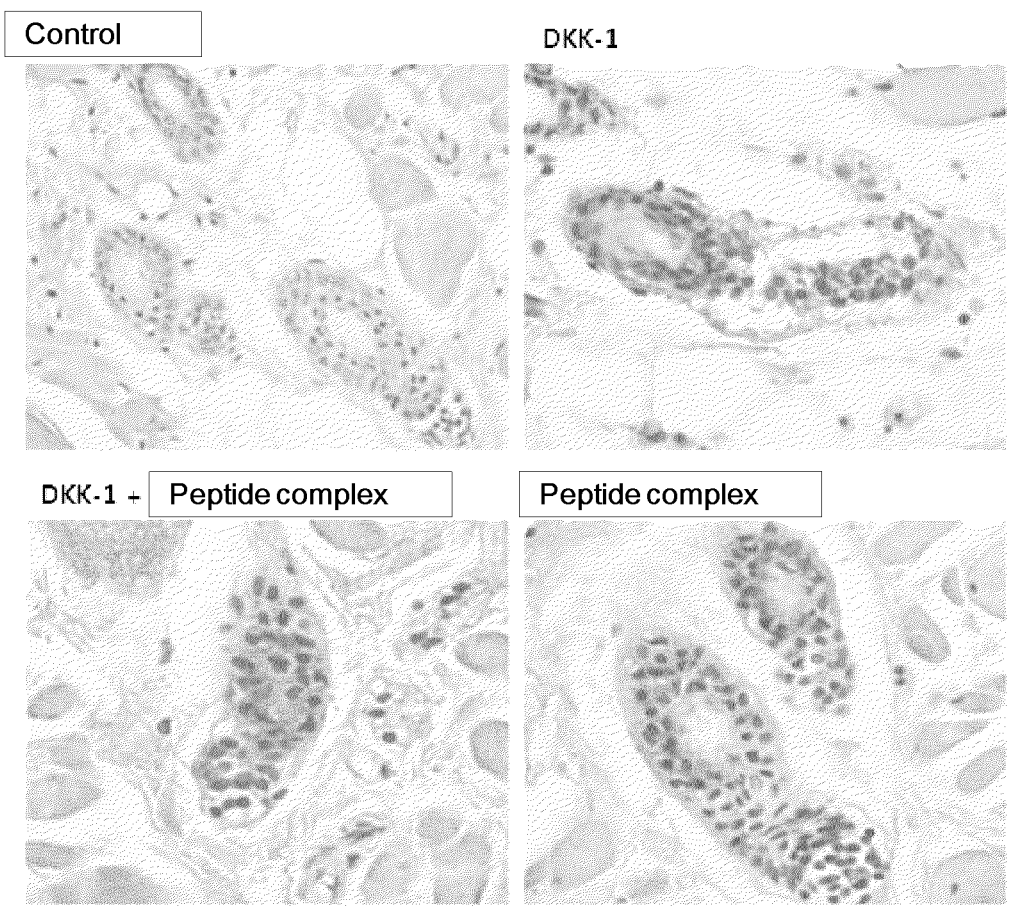
FIG. 13b is an immunostaining image representing that β-catenin expression in hair follicle during mouse hair follicle culture is enhanced by the peptide complex of the present invention.

FIG. 13b shows that DKK-1-induced inhibition of β-catenin was recovered by treatment with the peptide complex of the present invention. It could be confirmed that the expression of β-catenin in control are inhibited by DKK-1, whereas the expression of β-catenin simultaneously treated with DKK-1 and the present peptide complex are not suppressed but sharply elevated.

Figure 13C:
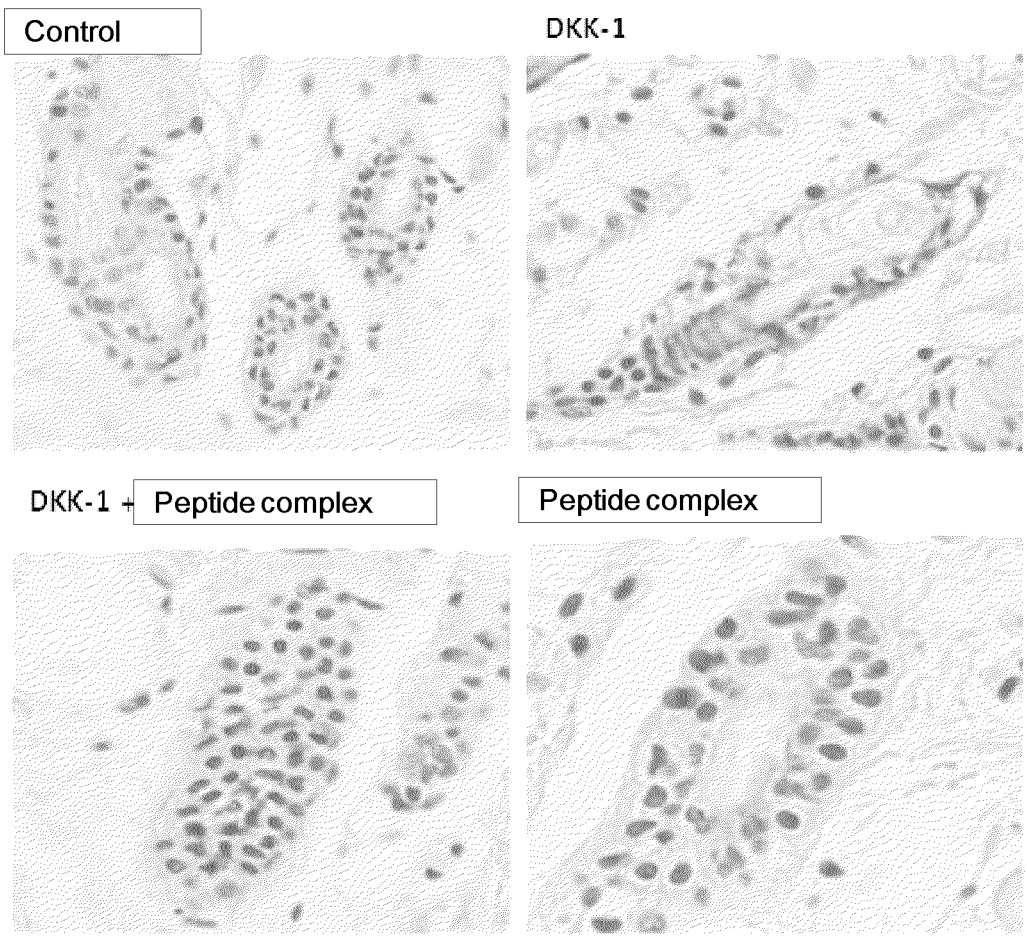
FIG. 13c shows an immunostaining image representing that WNT protein expression in hair follicle during mouse hair follicle culture is elevated by the peptide complex of the present invention.

As shown in FIG. 13c, the expression of WNT protein was inhibited by treating DKK-1 to control. However, the expression of WNT protein was enhanced by simultaneous treatment with DKK-1 and the present peptide complex. These results suggest that the peptide complex of the present invention efficiently facilitates not only proliferation of cells neighboring to hair but also production of hair follicles.

Figure 13D:
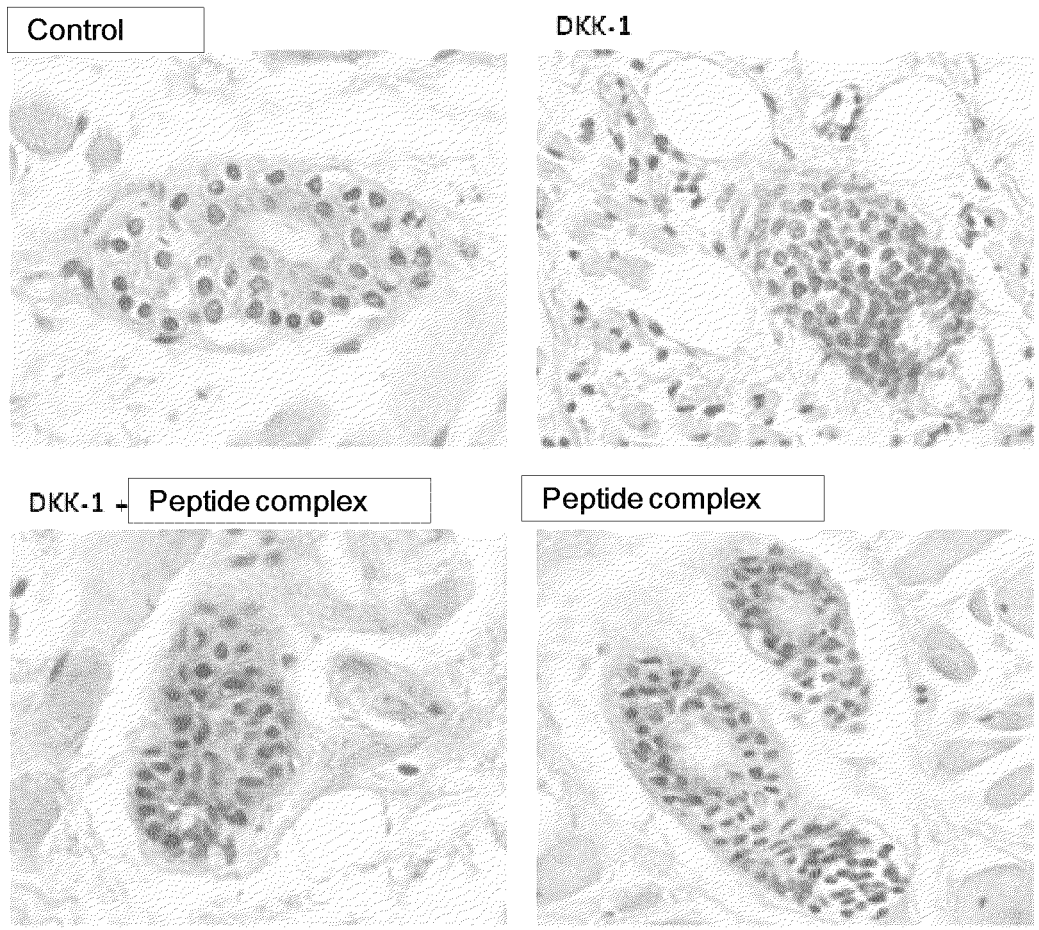
FIG. 13d is an immunostaining image representing that Ki-67 protein expression in hair follicle during mouse hair follicle culture is increased by the peptide complex of the present invention.

As illustrated in FIG. 13d, Ki-67 protein expression in hair follicle was suppressed by treating DKK-1 to control. Meanwhile, the expression of Ki-67 protein was elevated by simultaneous treatment with DKK-1 and the present peptide complex.

Taken together, these results represent that DKK-1 inhibits cell growth in hair follicles and even causes cell death to induce degeneration of hair follicle. Therefore, the degeneration of hair follicle induced by DKK-1 may be overcome by the peptide complex of the present invention. Consequently, it could be appreciated that the present peptide complex may promote proliferation and production of hair follicle cells.

Example 1

Preparation of Nano Peptides 50 mg of each peptide synthesized in preparation Examples was dissolved in 500 ml of distilled water by sufficient agitation. The peptide solution was mixed with 5 g lecithin, 0.3 ml sodium oleate, 50 ml ethanol and a small amount of oils, and its volume was adjusted with distilled water to 1 L. The resulting solution was subjected to a microfluidizer under high pressure for emulsification, thereby providing nanosomes having about 100-nm size. The nanosomes were prepared to have a final concentration of about 50 ppm and used as ingredients for cosmetics.

Formulation Example 1

Skin Softner

A skin softner comprising peptide-containing nanosomes prepared in Example 1 was formulated according to the following composition:

TABLE 2

| Ingredients | Content (wt %) |
| --- | --- |
| Peptide nanosome | 2.5 |
| 1,3-butylene glycol | 6.0 |

TABLE 2-continued

| Ingredients | Content (wt %) |
| --- | --- |
| Glycerin | 4.0 |
| PEG 1500 | 1.0 |
| Sodium hyaluronate | 1.0 |
| Polysorbate 20 | 0.5 |
| Ethanol | 8.0 |
| Preservative, pigment | Proper amount |
| Benzophenone-9 | 0.05 |
| Perfume | Minute amount |
| Distilled water | Residual amount |
| Total | 100 |

Formulation Example 2

Nutrient Cream

A nutrient cream comprising peptide-containing nanosomes prepared in Example 1 was formulated according to the following composition:

TABLE 3

| Ingredients | Content (wt %) |
| --- | --- |
| Peptide nanosome | 2.5 |
| Meadowfoam oil | 3.0 |
| Cetearylalcohol | 1.5 |
| Stearic acid | 1.5 |
| Glyceryl stearate | 1.5 |
| Liquid paraffin | 10.0 |
| Wax | 2.0 |
| Polysorbate 60 | 0.6 |
| Sorbitan sesquiolate | 2.5 |
| Squalane | 3.0 |
| 1,3-butylene glycol | 3.0 |
| Glycerin | 5.0 |
| Triethanol amine | 0.5 |
| Tocopheryl acetate | 0.5 |
| Preservative, pigments | Proper amount |
| Perfume | Proper amount |
| Distilled water | Residual amount |
| Total | 100 |

Formulation Example 3

Nutrient Liquid

A nutrient liquid comprising peptide-containing nanosomes prepared in Example 1 was formulated according to the following composition:

TABLE 4

| Ingredients | Content (wt %) |
| --- | --- |
| Peptide nanosome | 2.5 |
| 1,3-butylene glycol | 4.0 |
| Glycerin | 4.0 |
| Cetearyl alcohol | 0.8 |
| Glyceryl stearate | 1.0 |
| Triethanol amine | 0.13 |
| Tocopheryl acetate | 0.3 |
| Liquid paraffin | 5.0 |
| Squalane | 3.0 |
| Makadamianut oil | 2.0 |
| Polysorbate 60 | 1.5 |
| Sorbitan sesquiolate | 0.5 |
| Carboxyvinyl polymer | 1.0 |

Formulation Example 4

Essence

An essence comprising peptide-containing nanosomes prepared in Example 1 was formulated according to the following composition:

TABLE 5

| Ingredients | Content (wt %) |
| --- | --- |
| Peptide nanosome | 2.5 |
| Glycerin | 10.0 |
| 1,3-butylene glycol | 5.0 |
| PEG 1500 | 2.0 |
| Allantoin | 0.1 |
| DL-panthenol | 0.3 |
| EDTA-2Na | 0.02 |
| Hydroxyethyl cellulose | 0.1 |
| Sodium hyaluronate | 8.0 |
| Carboxyvinyl polymer | 0.2 |
| Triethanol amine | 0.18 |
| Octyldodeceth-16 | 0.4 |
| Ethanol | 6.0 |
| Perfume, preservative, pigments | Proper amount |
| Distilled water | Residual amount |
| Total | 100 |

Formulation Example 5

Hair Serum

A hair serum comprising peptide-containing nanosomes prepared in Example 1 was formulated according to the following composition:

TABLE 6

| Ingredients | Content (wt %) |
| --- | --- |
| Peptide nanosome | 1 |
| Glycerin | 10.0 |
| 1,3-butylene glycol | 5.0 |
| PEG 1500 | 2.0 |
| Allantoin | 0.1 |
| DL-panthenol | 0.3 |
| EDTA-2Na | 0.02 |
| Hydroxyethyl cellulose | 0.1 |
| Sodium hyaluronate | 8.0 |
| Carboxyvinyl polymer | 0.2 |
| Triethanol amine | 0.18 |
| Octyldodeceth-16 | 0.4 |
| Ethanol | 6.0 |
| Perfume, preservative, pigments | Proper amount |
| Distilled water | Residual amount |
| Total | 100 |

Formulation Example 6

Hair Toner

A hair toner comprising peptide-containing nanosomes prepared in Example 1 was formulated according to the following composition:

TABLE 6

| Ingredients | Content (wt %) |
| --- | --- |
| Peptide nanosome | 1 |
| Glycerin | 2.0 |
| 1,3-butylene glycol | 2.0 |
| PEG 1500 | 2.0 |
| Allantoin | 0.1 |
| DL-panthenol | 0.3 |
| EDTA-2Na | 0.02 |
| Sodium hyaluronate | 8.0 |
| Carboxyvinyl polymer | 0.2 |
| Triethanol amine | 0.18 |
| Octyldodeceth-16 | 0.4 |
| Ethanol | 10.0 |
| Perfume, preservative, pigments | Proper amount |
| Distilled water | Residual amount |
| Total | 100 |

Having described a preferred embodiment of the present invention, it is to be understood that variants and modifications thereof falling within the spirit of the invention may become apparent to those skilled in this art, and the scope of this invention is to be determined by appended claims and their equivalents.

---

What is claimed is:

1. A peptide comprising the amino acid sequence of SEQ ID NO:1.

2. The peptide of claim 1, wherein the peptide is derived from a human WNT10.

3. The peptide of claim 1, wherein the peptide facilitates cell proliferation in keratinocytes and fibroblasts.

4. The peptide of claim 1, wherein the peptide promotes fibronectin expression.

5. The peptide of claim 1, wherein the peptide transfers β-catenin into a nucleus.

6. A method for treating hair loss, comprising administering to a subject a composition comprising the peptide of claim 1 as an active ingredient.

7. The method of claim 6, wherein the composition further comprises a peptide having the amino acid sequence of (i) SEQ ID NO:2, (ii) SEQ ID NO:3 and SEQ ID NO:4 linked by an amino acid or a peptide linker, or (iii) both peptides defined by (i) and (ii).

8. The method of claim 6, wherein prevention or the treatment of the hair loss is promotion of hair growth or production of hair.

9. A method for promoting fibroblast or keratinocyte proliferation, or elevating the level of fibronectin, comprising administering to a subject a composition comprising the peptide of claim 1 as an active ingredient.

10. The method of claim 9, wherein the composition further comprises a peptide having the amino acid sequence of (i) SEQ ID NO:2, (ii) SEQ ID NO:3 and SEQ ID NO:4 linked by an amino acid or a peptide linker, or (iii) both peptides defined by (i) and (ii).

11. The method of claim 9, wherein the administration of the composition results in a decrease in the number and/or severity of wrinkles, an increase in skin elasticity, an increase in skin moisture, accelerated wound healing, or regeneration of skin.

12. A method for treating a WNT10 signal transduction pathway-related disorder, comprising administering to a subject a composition comprising the peptide of claim 1 as an active ingredient.

13. The method of claim 12, wherein the composition further comprises a peptide having the amino acid sequence of (i) SEQ ID NO:2, (ii) SEQ ID NO:3 and SEQ ID NO:4 linked by an amino acid or a peptide linker, or (iii) both peptides defined by (i) and (ii).

14. The method of claim 12, wherein the WNT10 signal transduction pathway-related disorder comprises a bone disorder or a tumor disorder.

15. The method of claim 14, wherein the bone disorder is selected from the group consisting of a disease associated with bone development, a bone fracture, a senile bone loss, chondrodystrophia, hypercalcemia, hyperostosis, osteogenesis imperfect, osteomalacia, osteomyelitis, osteoporosis, Paget's disease of bone, osteoarthritis and rachitis.

16. A method for treating a DKK-1 protein-induced disorder, comprising administering to a subject a composition comprising the peptide of claim 1 as an active ingredient.

17. The method of claim 16, wherein the composition further comprises a peptide having the amino acid sequence of (i) SEQ ID NO:2, (ii) SEQ ID NO:3 and SEQ ID NO:4 linked by an amino acid or a peptide linker, or (iii) both peptides defined by (i) and (ii).

18. The method of claim 16, wherein the DKK-1 protein-induced disorder comprises diabetes or muscle recovery or regeneration.

19. The method of claim 18, wherein the diabetes is associated with insulin resistance and hypoglycemia.

\* \* \* \* \*

SEQUENCE LISTING

<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: WNT10-derived peptide 1

<400> SEQUENCE: 1

Arg Gln Thr Arg Val Gln Arg Cys His Cys
1               5                   10

```
<210> SEQ ID NO 2
<211> LENGTH: 10
<212> TYPE: PRT
<213> ORGANISM: Artificial Sequence
<220> FEATURE:
<223> OTHER INFORMATION: keramin2-derived peptide 1

<400> SEQUENCE: 2

Tyr Lys Ser Lys Lys Gly Gly Trp Thr His
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Nokkin-derived peptide 1

<400> SEQUENCE: 3

Glu Leu Ile Glu His
1               5

<210> SEQ ID NO 4
<211> LENGTH: 4
<212> TYPE: PRT
<213> ORGANISM: Artificial Sequence
<220> FEATURE:
<223> OTHER INFORMATION: Nokkin-derived peptide 1

<400> SEQUENCE: 4

Arg Pro Ala Asp
1
```